United States Patent
Sahagian et al.

(10) Patent No.: US 6,299,438 B1
(45) Date of Patent: Oct. 9, 2001

(54) ORTHODONTIC ARTICLES HAVING A LOW-FRICTION COATING

(75) Inventors: Richard Sahagian, Burlington; Anthony J. Armini, Manchester-by-the-Sea, both of MA (US)

(73) Assignee: Implant Sciences Corporation, Wakefield, MA (US)

( * ) Notice: Subject to any disclaimer, the term of this patent is extended or adjusted under 35 U.S.C. 154(b) by 0 days.

(21) Appl. No.: 09/162,546

(22) Filed: Sep. 29, 1998

Related U.S. Application Data

(60) Provisional application No. 60/060,450, filed on Sep. 30, 1997.

(51) Int. Cl.$^7$ ....................................... A61C 3/00
(52) U.S. Cl. ........................... 433/6; 433/8; 433/7; 433/2
(58) Field of Search .................... 433/2, 6, 7, 8, 433/18, 20, 23; 29/896.1, 896.11

(56) References Cited

U.S. PATENT DOCUMENTS

| | | |
|---|---|---|
| 4,197,643 | 4/1980 | Burstone et al. . |
| 4,626,209 | 12/1986 | Tsai et al. . |
| 4,818,226 | 4/1989 | Berendt et al. . |
| 4,902,224 | 2/1990 | Collins et al. . |
| 4,946,387 | 8/1990 | Adell . |
| 5,032,080 | 7/1991 | Hakansson et al. . |
| 5,080,584 | 1/1992 | Karabin . |
| 5,167,499 | 12/1992 | Arndt et al. . |
| 5,167,500 | 12/1992 | Miura . |
| 5,232,361 * | 8/1993 | Sachdeva et al. ........................ 433/8 |
| 5,288,230 | 2/1994 | Nikutowski et al. . |
| 5,344,315 | 9/1994 | Hanson . |
| 5,380,196 * | 1/1995 | Kelly et al. ............................... 433/8 |
| 5,399,088 | 3/1995 | Mechley . |
| 5,454,716 | 10/1995 | Banerjee et al. . |
| 5,624,258 | 4/1997 | Wool . |
| 5,816,801 * | 10/1998 | Farzin-Nia et al. ..................... 433/8 |

FOREIGN PATENT DOCUMENTS

J6 3200752 * 8/1988 (JP) ......................................... 433/8

OTHER PUBLICATIONS

Takekawa et al., "Combined Use of Percutaneous Transluminal Laser Irridation and Balloon Dilatation Angioplasty in the Treatment of Arteriosclerotic Stenoses of Iliac and Femoral Arteries," Nippon ACTA Radiology, vol. 45 (8), pp. 1167–1169 (1985).

* cited by examiner

Primary Examiner—Jeffrey A. Smith
(74) Attorney, Agent, or Firm—Foley, Hoag, Eliot LLP

(57) ABSTRACT

A dental article coated with a friction-reducing coating and methods for coating dental articles are disclosed. In one embodiment, the dental device first is coated with an adhesion layer, followed by application of a friction-reducing coating. The friction-reducing coating is selected to create a hard, inert, friction-reducing layer on the device. The presence of the continuous outer coating of on the device reduces adhesive wear and friction on the device, and significantly improves its frictional properties.

28 Claims, 2 Drawing Sheets

ORTHODONTIC ARTICLES HAVING A LOW-FRICTION COATING

CROSS-REFERENCE TO RELATED APPLICATION

This application is based on and claims priority to co-pending U.S. provisional patent application serial No. 60/060,450, filed Sep. 30, 1997. The provisional application is hereby incorporated herein by reference.

FIELD OF THE INVENTION

This invention relates to the field of dental articles, such as orthodontic archwires and brackets. More specifically, the invention relates to dental articles and brackets having a hard metallic friction-reducing coating.

BACKGROUND OF THE INVENTION

Orthodontic tooth movement in mechanotherapy depends on the ability of a clinician to use controlled mechanical forces to stimulate biologic responses within the paradental tissues surrounding the roots of treated teeth. The most common orthodontic technique consists of an edgewise bracket that slides along an archwire. The sliding arch-guided system, or sliding mechanics, can be influenced by counteracting frictional forces at the interface of the bracket, archwire, and ligature. Thus, the basic principle of orthodontic appliances in the continuous archwire technique is to apply mechanical forces on teeth so that movement will occur in every desirable spatial direction. The forces are applied during the various stages of treatment by a variety of appliances, which include several kinds of archwire, ligatures, and bands.

Friction among appliances used for orthodontic correction of teeth is recognized by clinicians as a hindrance to tooth movement. Friction reduces the effective force, which is applied to the tooth from the wire. In the case of sliding mechanics, excessive friction, brought about by the angle between the wire and the slot of the bracket, slows tooth movement down substantially or even halts it. It would be of great clinical advantage to minimize this friction so that the clinician can accurately estimate the amount of force transmitted to each tooth. Unimpeded tooth movement would reduce the time needed for treatment, thereby reducing the risks of adverse effects of wearing orthodontic braces on the teeth and surrounding tissues. It would be desirable to minimize the effect of any factors over which a clinician has no control, including the amount of friction between the archwire and the bracket.

There are several variables that affect the amount of friction between orthodontic appliances, most prevalent of which is the composition of the wire and bracket material. The problem of friction is compounded by the desire for aesthetically pleasing appliances such as ceramic brackets, which have greater friction toward all types of archwires than stainless steel brackets. Archwires made of beta-titanium have desirable properties such as good flexibility, spring force and biocompatibility, and are the only orthodontic wires containing no nickel. However, these materials are soft, have poor frictional characteristics and are very susceptible to adhesive wear. Orthodontic tooth movement in mechanotherapy depends on the ability of a clinician to use controlled mechanical forces to stimulate biologic responses within the tissues surrounding the roots of treated teeth, most commonly by way of an edgewise bracket sliding along an archwire. Frictional forces at the interface of the bracket, archwire, and ligature can hinder these sliding mechanics.

The friction coefficients between bracket and various wire materials have been measured extensively. Wires made out of such popular shape memory materials such as titanium-molybdenum alloy (TMA) and Ni—Ti (nickel-titanium) alloys tend to be softer than stainless steel and tend to have higher coefficients of friction against stainless steel than does stainless steel itself, which has a high coefficient of friction. This is true particularly at high (~80 N) normal forces.

Coating thin films of various materials onto archwires has been previously suggested as a way to reduce friction and to improve their aesthetic appearance. U.S. Pat. No. 5,288,230 to Nikutowski et al. describes applying a coating of diamond-like carbon (DLC) onto archwires to serve as a barrier to diffusion of nickel and chromium from the wire, which causes allergic reactions in the patient. The DLC coatings also provide a hard, friction-reducing surface. The appearance of the DLC films, however, ranges from black to interference rainbow colors, and is not aesthetically pleasing. U.S. Pat. No. 5,454,716 to Banerjee et al. describes a coating of a plastic-ceramic composite, which is aesthetically pleasing, but is susceptible to localized abrasion over time.

Ion implantation has been used to modify orthodontic materials with the goal of reducing friction. For example, alumina, which is a commonly used ceramic in bracket manufacture, has been implanted with titanium with a resulting decrease in its coefficient of friction with beta-titanium wire. (Kusy et al., *Dental Material* 8:167–172, 1992). Friction reduction was observed for alumina flats coated with DLC. (R. P. Kusy et al., (1993) J. Am. Ceram. Soc., 76[2], 336–342 Implantation of beta-titanium wires with nitrogen reduced the friction due to formation of hard titanium oxy-nitride on the wire. (R. P. Kusy et al., Nanda, 215–221 (1993); R. P. Kusy et al., Dental Mater., 8, 167–172 (1992); R. P. Kusy et al., (1993) J. Am. Ceram. Soc., 76[2], 336–342).

SUMMARY OF THE INVENTION

The present invention relates to dental articles having improved properties and to systems and methods for coating dental articles to improve their mechanical and physical properties. The dental articles of the present invention generally comprise metal and/or ceramic articles designed for temporary or permanent placement in the mouth having a hard friction-reducing coating. The article further may comprise at least one interlayer between the article and the outer, friction-reducing coating. In some embodiments of the invention, the presence of the interlayer improves adhesion of the outer, friction-reducing layer to the surface of the article.

The articles may comprise, for example, orthodontic devices such as archwires, brackets, retainers and palate expanders. The adhesion layer comprises any metallic material which has the effect of improving adhesion of the outer, friction-reducing layer to the article. The friction reducing coating comprises a biocompatible metallic or ceramic coating capable of reducing the surface friction of the coated article (compared to the uncoated article) so that pieces of the dental article which are connected together and cooperate with each other, e.g., archwires and brackets, can slide past each other more easily, thereby allowing for easier and more precise adjustment by the orthodontist or dentist. The coating preferably also has the properties of being resistant to mechanical wear and sufficiently inert to resist degradation in the harsh environment of the mouth.

The method of the invention generally comprises applying a friction-reducing coating to a metal and/or ceramic dental article. In a preferred embodiment of the present method, the article first is coated with an adhesion layer or interlayer, followed by deposition of an outermost, friction-reducing coating. The adhesion layer can be any metallic material which has the effect of improving the bonding of the outer, friction-reducing layer to the substrate. The adhesion layer and the friction reducing coating may be applied by any technique which is useful for depositing metallic and/or ceramic coatings onto metallic or ceramic substrates, for example, sputtering, chemical vapor deposition, ion beam enhanced deposition, plasma-assisted vapor deposition, cathodic arc deposition, ion implantation and evaporation.

The continuous coating on the article reduces adhesive wear and friction on the article, and the frictional and wear properties of the article thus are significantly improved.

DETAILED DESCRIPTION OF THE INVENTION

Figure 1:
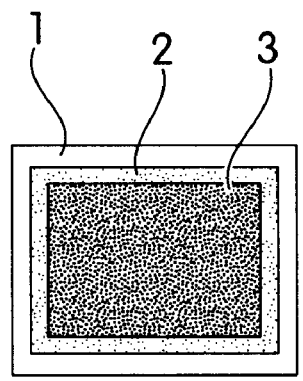
FIG. 1 illustrates a cross-sectional view of a coated archwire according to one embodiment of the present invention.

The invention comprises a dental article having a friction-reducing coating, and methods for coating a dental article with a friction-reducing coating.

The dental article comprises a metallic or ceramic article which is placed temporarily or permanently in the mouth of an individual. Such articles include, for example, orthodontic appliances such as archwires, brackets, retainers and palate expanders. The articles may be comprised of any material suitable for use in dental devices, for example, metals or ceramics, including stainless steel, titanium, titanium-molybdenum alloy (TMA), beta-titanium, nitinol, alumina, zirconia, nickel-titanium, and alloys and blends of these materials. Beta-titanium, stainless steel and nickel-titanium alloys are currently preferred archwire materials, and stainless steel and alumina are currently preferred bracket materials.

Articles of the present invention preferably are coated with a hard metallic and/or ceramic coating which improves the mechanical, physical and aesthetic properties of the article, in particular, reduces its surface friction. Materials useful for the friction-reducing coating include hard, relatively inert metals which do not tend to form oxides in the environment of the mouth and inert ceramic materials (which are oxides). Metals useful for this purpose include iridium, platinum, palladium, rhodium, rhenium, gold, silver and blends or alloys of these metals. Iridium and platinum are particularly preferred because they provide a hard, inert, friction-reducing outer layer on the article.

In a preferred embodiment, the article further comprises an adhesion layer or interlayer between the outer, friction-reducing coating and the article. The adhesion layer may be a metallic material which is capable of adhering strongly to the surface of the article and of bonding well to the outer, friction-reducing coating, thereby providing a strong bonding layer between the outer friction-reducing coating and the substrate. Materials useful for this purpose include chromium, titanium, nickel, palladium and blends or alloys of these materials. Chromium and blends of chromium-iridium or palladium-iridium currently are preferred materials for use in the adhesion layer.

The coated device of the invention also may include one or more additional intermediate layers between the adhesion layer and the outer, friction-reducing layer. The intermediate layer(s) preferably comprise a metallic material selected from the group consisting of chromium, titanium, nickel, palladium and blends or alloys of these materials, including chromium-iridium or palladium-iridium blends.

The invention also comprises a method of making a coated dental article having a hard, friction-reducing outer coating. The method comprises depositing a metallic or ceramic coating onto the surface of the article thereby forming a continuous, integral layer having reduced frictional properties compared to the uncoated article. In a preferred embodiment of the present method, an adhesion layer or interlayer first is applied to the substrate, followed by deposition of the outer, friction-reducing layer. In a currently preferred embodiment, the article first is coated with a thin layer of chromium as an adhesion layer, followed by deposition of a thicker coating of iridium as the friction-reducing layer. The adhesion layer and the friction reducing coating may be applied by any technique which is useful for depositing metallic and/or ceramic coatings onto metallic or ceramic substrates, for example, sputtering, chemical vapor deposition, ion beam enhanced deposition, plasma-assisted vapor deposition, cathodic arc deposition, ion implantation and evaporation. Currently preferred methods of applying the coating include unbalanced magnetron sputtering and hollow cathode sputtering. Coatings applied according to the invention are adherent and can be applied by a process that does not damage the dental article or its shape-memory properties.

Iridium and platinum are currently preferred for use as friction-reducing coatings in the present invention because they are inert, dense and hard metals that, unlike stainless steel, have few native oxides and form alloys with very few metals. Therefore, they are subject to less friction against stainless steel. Iridium is particularly preferred for use in the present invention for the following reasons. Iridium is commonly used in intravenous biomedical applications and has an established history as a biocompatible material. Iridium also exhibits good wettability, allowing the mouth's saliva to act as a lubricant between the components of the dental device, e.g., between the archwire and the bracket. Iridium coatings on an archwire or other article provide enhanced resistance to corrosion when exposed to the oral environment. Iridium coatings are advantageous in that such coatings are less expensive than diamond-like carbon coatings and ion implanted devices. Iridium coated articles also have the bright appearance of polished chrome which is more aesthetically pleasing than diamond-like carbon coatings and ion implanted surfaces, and will maintain the polished chrome look, even in the harsh oral environment. Coating the device with iridium provides the article with better, more uniform frictional properties than those present on the uncoated surface. Achieving correct stoichiometry is not necessary because iridium is elemental. Furthermore, iridium coatings applied by an unbalanced magnetron sputtering process encapsulate the article and become a barrier to diffusion of undesirable substances which may be present in the article, such as nickel, which may have an adverse effect on some patients.

Figure 2:
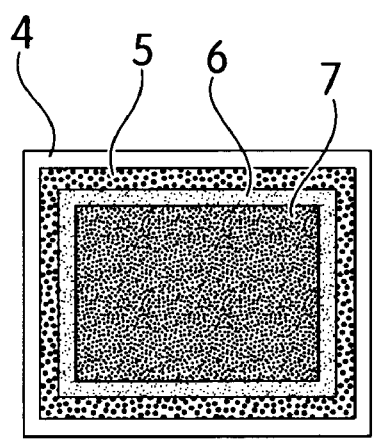
FIG. 2 illustrates a cross-sectional view of a coated archwire according to another embodiment of the present invention.

Turning now to the Figures, FIG. 1 illustrates a cross-sectional view of an archwire 3 having an iridium layer 1 adhered with a thin chromium layer 2. FIG. 2 illustrates a cross-sectional view of an archwire 7 in which an iridium layer 4 is adhered by a mixed layer of iridium and chromium 5 on top of a chromium thin layer 6 on the archwire 7. The archwire can be made of any metal useful for this purpose. Preferably, the archwire substrates 3 and 7 are stainless steel, beta-titanium, or nickel-titanium alloy.

Figure 3:
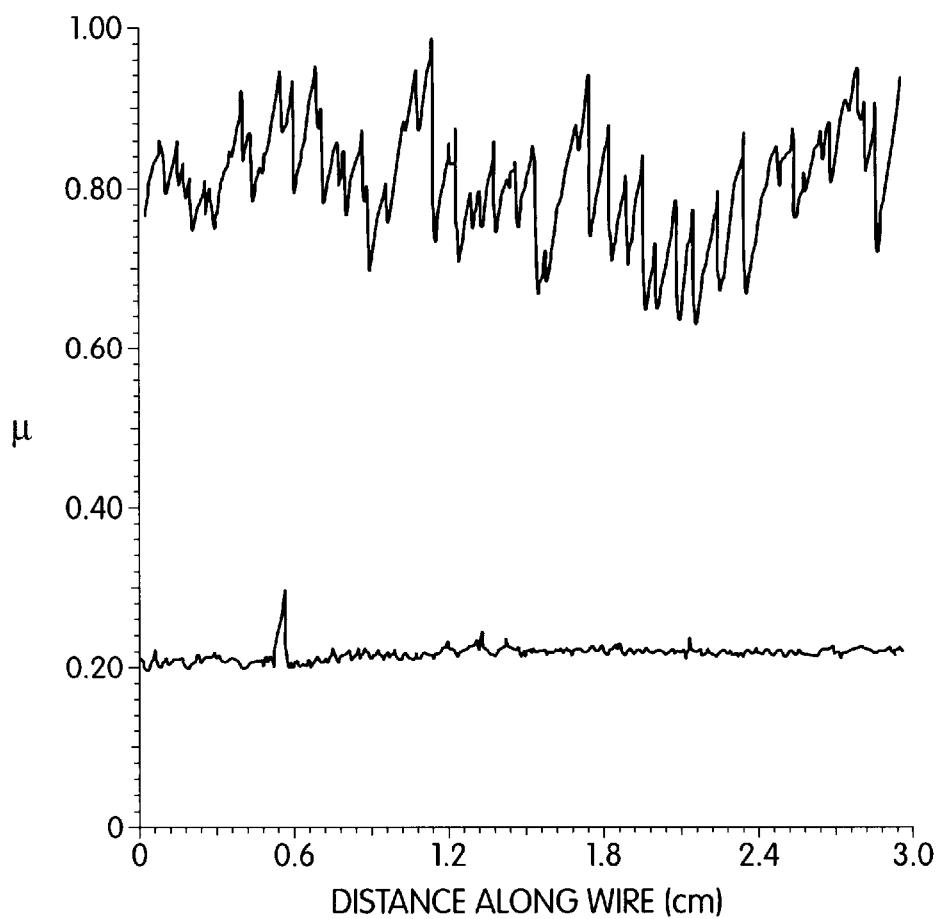
FIG. 3 shows friction testing results done on an uncoated beta-titanium archwire and the friction testing results done on an iridium-coated beta titanium archwire according to an embodiment of the present invention.

FIG. 3 shows friction testing results performed on an uncoated beta-titanium archwire (the upper trace 10) compared to the friction testing results performed on an iridium-coated beta titanium archwire (the lower trace 20). The coated archwire exhibited a much lower coefficient of friction.

Figure 4:
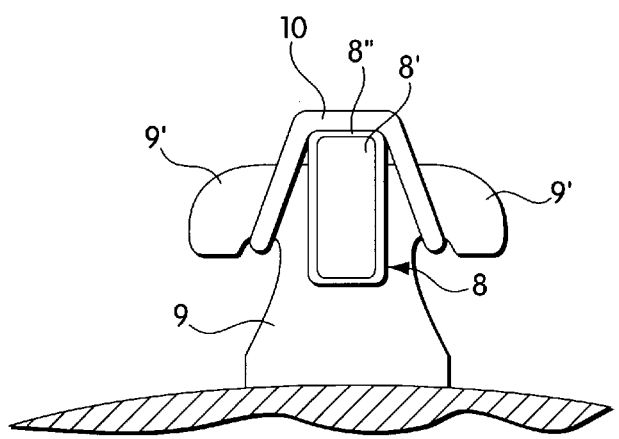
FIG. 4 shows a bracket and archwire assembly in place on a tooth in which the assembly has a coated archwire according to the invention.

FIG. 4 shows shows a bracket and archwire assembly in place on a tooth wherein archwire 8 comprises the base archwire 8' and low-friction coating 8" held in place by brackets 9, 9' and ligature wire 10.

In a preferred embodiment of the present method, the article is cleaned to remove surface contamination from the substrate before the adhesion layer or friction-reducing layer is coated onto the substrate. Any cleaning technique which is effective in removing oxidation, oils and other contaminants from the surfaces of the article can be used. The cleaning process may be an ion sputtering technique, for example, a glow discharge technique or an ion bombard from a Kaufman source or other ion source. The removal of the surface contaminants provides a better surface for application of the adhesion layer or friction-reducing layer onto the substrate.

In a preferred embodiment of the present method, the adhesion layer is applied onto the substrate as a primer layer in the range of about 100–10,000 Angstroms (Å) thick. The adhesion layer preferably is applied by sputtering at a bias of approximately 1–10,000 volts (V). The sputtering process preferably is carried out in the presence of an inert gas, such as argon, at a pressure of about 0.1–100 mTorr. In a currently preferred embodiment, the layer is from about 500 to about 5000 Angstroms in thickness. Chromium, or a blend of chromium-iridium, currently is the preferred material for use as the adhesion layer. However, other suitable metallic materials may be used.

The outer, friction-reducing coating then is applied over the adhesion layer. In a preferred embodiment, the outer, friction-reducing coating has a thickness of about 0.1 microns ($\mu$) to about 5 microns. The iridium layer also can be applied by any of the techniques suitable for applying a metallic coating to a substrate. In the currently preferred embodiment, the outer, friction-reducing coating is applied by sputtering, at a bias of about 1–10,000 volts (V) in the presence of an inert gas at a pressure of about 0.1–100 mTorr. In a currently preferred embodiment, the coating is from about 0.5 to about 3 microns thick. Iridium is the currently preferred material for the friction-reducing layer. In the currently preferred embodiment, the growth rates for the metal layers were approximately 100 Angstroms per minute and approximately 1 micron per hour for chromium and iridium, respectively.

In one embodiment, improved adhesion of the iridium outer layer may be obtained when part of the adhesion layer is blended with iridium. A blended coating can be deposited, for example, by a applying the adhesion coating and the friction-reducing coating simultaneously for at least part of the application time and by controlling the deposition rates of each. For example, using a sputtering technique, two sputter heads are used, one for the metal which will form the adhesion layer (e.g., chromium) and one for the metal which will form the friction-reducing layer (e.g., iridium). A blended layer can be formed by first applying a portion of the chromium adhesion layer, then ramping up the deposition rate for the iridium metal while ramping down the deposition rate for the chromium. The resulting coating will be a base chromium layer in contact with the surface of the article followed by a blended portion in which the ratio of chromium to iridium in the blend gradually decreases followed by a pure iridium outer layer. Although chromium and iridium are used in the example illustrated above, it will be clear to those skilled in the art that other materials having the desired characteristics, which are described herein, can be used.

The following examples are provide to further illustrate the invention and are not intended to be limiting in any way.

EXAMPLES

Example 1

Test samples were made using an unbalanced magnetron sputtering process to first apply a thin primer layer of chromium to beta-titanium archwires, followed by a thicker layer of iridium, according to the following procedure. Round archwires of about 0.023-inch diameter and rectangular wires of about 0.017×0.025 inches were used ("Beta-III", from Ultimate Wireforms; Bristol, Conn.). A fifteen-minute glow discharge first was carried out to clean surface oxides from the archwires. A bias of 500 volts was applied to the metal substrates in an atmosphere of argon at 3 millitorr. Chromium was sputtered to a thickness of 700 Å. Iridium was then sputtered at 200 watts in 4 millitorr of argon to a 1, 1.5, or 2 micron thickness. Substrate temperature was not controlled.

The sliding friction was compared between archwires coated as described above and uncoated archwires using a single pull tribometer. This device measures the frictional force along the wire. FIG. 3 shows the friction vs. distance traveled for both the iridium coated and bare archwires. Each archwire was pulled through the apparatus for 3 cm in length. The upper trace 10 of FIG. 3 shows the results for the uncoated archwire. The amplitude of variation of the frictional force along the wire was great, by a factor as high as 2.5. Interspersed among these large variations were areas of much smaller variation. The frictional performance of the uncoated beta-titanium archwire was non-uniform and erratic. This condition is often called "stick-slip." By contrast, the lower trace 20 of FIG. 3 for the iridium-coated wire shows much lower variability in the frictional force along its length, and a much lower average coefficient of friction. The iridium-coated archwire had much more uniform friction, that is, it does not exhibit stick-slip, and better performance than the uncoated wire in an orthodontic appliance.

Example 2

Iridium metal was coated onto stainless steel brackets (A-Company, San Diego, Calif.) and TMA archwires ("Beta-III", from Ultimate Wireforms; Bristol, Conn.) using an unbalanced magnetron sputtering process. The wires and brackets to be coated first were cleaned by an argon glow technique. The substrates were rotated to promote film uniformity. The deposited layers consisted of chromium followed by iridium so that the chromium served as an adhesion layer.

The surface of the beta-titanium wires had a rough, lamellar appearance under an optical microscope and iridium (Ir) films deposited on them conformed to that surface. The total thickness of the Ir films was 1.5 microns, which increased the overall thickness of the wire by 3 microns.

The coated brackets and archwires were subjected to a series of tests. For testing, brackets were affixed to aluminum flats, which were, in turn fastened to the pull testing apparatus. A commercial ethylcyanoacrylate adhesive (Krazy® Glue) was used to bond the bracket to the flat. An aluminum flat was prepared with a 0.015" and to align the bracket to the center of the flat, to ensure that the bracket slot would hold the wire perpendicular to the length of the flat. The wires, which had an inherent curve, were ligated so that the curve was concave to the left. The wires were bent with hooks facing the left as well, in order to join them to the spring on the load cell assembly of the pull testing apparatus.

Brittleness Test

The wires were tested for brittleness according to the following procedure. The wire was grasped with a pair of pliers perpendicular to the length of the wire. The wire was bent 90° at the point where the pliers hold the wire. This constituted one bend. The wire then was bent back to center (straightening out the wire), that constituted a second bend. The wire was then bent 90° in the opposite direction from the first bend, thereby making a third bend. The wire was straightened out again, (bent back to center, as per the second bend) making a fourth bend. These processes are repeated until the wire breaks, with the number of bends required to break the wire counted at the bend that actually broke the wire, minus one. Untreated beta-titanium (TMA) wires could withstand 4–5 such bends before breaking. The Ir-coated-TMA wires behaved as well as the bare TMA wires when subjected to the bend test described above.

Reproducibility of Ligating Wires to Brackets

Reproducibility in ligating wires to brackets was tested. Tying ligatures was done according to well-accepted protocols. Pre-formed 0.010" stainless steel ligature wires (Ultimate Wireforms) were used. The ligature was grasped by a pair of hemostats, which were then closed around the wire. The ligature wire's loop was placed around the bracket and pulled tight so that the wire bent to fit flush under the hooked parts of the bracket. The wire was given six half-twists by the hemostats, followed by bending the twisted part of the wire upward so that it was about 30° from the normal. The hemostats were disconnected from the ligature, then reconnected to the ligature near the bottom of the helical twist, between the first and second twists of the spiral that had been made by twirling the ligature wire. A torque-regulating screwdriver set at 16 oz-in (Utica) was then attached to the hemostats and further twirling was done until the clutch of the screwdriver slipped. This occurred between 1½ and 2½ full turns.

Diamond Scratch Testing

Adhesion of the coatings to the substrates was measured by a scratch test, which consisted of deliberately scratching the coating with a diamond stylus at increasing loads until delamination of the film was observed through an optical microscope. Examination of the fracture by optical microscope was used to define the type of failure as either "adhesive" or "cohesive" according to whether the failure was at the interface or within the coating itself respectively. For this test a reciprocating tribometer built by Implant Sciences, Inc. (Wakefield, Mass.) was used with a diamond stylus and increasing loads to a maximum of 40 N, using a lever arm. The tub containing the flat sample is moved under the diamond stylus, and the surface of the flat is scratched. For scratch testing the wires, a special mount was made, with a slot designed to fit the wire snugly. The diamond stylus is then aligned carefully to the wire, and a lead weight with the desired normal force is placed atop the diamond stylus. The wire is held in place while the diamond stylus mount is moved along the wire, making the scratch. The results are described below under the heading "Adhesion and Friction Testing Results."

Wire Pull Testing

Wire/bracket pull testing was done on a modified ISC tribometer. The wire was hooked onto the spring, which was connected to the load cell. The bracket, ligatured to the wire and mounted on an aluminum coupon as described above, was pulled along for 3 minutes at 1 cm/min. The normal force used for friction measurements was unknown, since it was derived from the ligatures. The values of coefficient of friction recorded are relative, and the "load" was set to 434 g on the ISC tribometer for all friction measurements. This was to normalize coefficient of friction readings for the control couple (bare stainless steel bracket/bare TMA wire) in such a way as to ensure that the highest readings would only rarely exceed 1.

The coefficients of friction measured were kinetic, and tests were performed both without foreign substances such as saliva, which is known to have lubricating effects on orthodontic appliances, and with Oralube artificial saliva (Preventative Dentistry Support Center, VA Medical Center, Houston, Tex. 77030) as a lubricant to simulate natural oral conditions. Samples for this second set of tests were prepared in a similar fashion to the dry samples, but before the wire was ligatured, a large drop of the Oralube was applied to the bracket to immerse it. The wire was wetted with Oralube as well, just before being placed into the bracket's slot. The ligaturing was then done as described above. This is better wetting and lubrication than that which would occur in the mouth on a daily basis and represents a best-case scenario. Friction coefficients were recorded, plotted, and averaged. The results are described below under the heading "Adhesion and Friction Testing Results."

Adhesion and Friction Testing Results

Iridium was coated onto brackets and beta-titanium wires to a nominal thickness of 1.5 microns as described above. The values for the coefficients of friction derived from wire pull testing under dry conditions were obtained by averaging thirty individual wire pull tests. The results are shown in Table 1a.

TABLE 1a

Coefficients of Friction for Various Bracket/Wire Couples, Dry Conditions

| Couple # | Bracket | Wire | Measured coefficient of friction (m)(Average ± Std. Dev.) |
|---|---|---|---|
| 1 | Bare stainless steel | Bare beta-titanium | 0.589 ± 0.236 (control) |
| 2 | Ir-coated stainless steel | Bare beta-titanium | 0.580 ± 0.229 |
| 3 | Bare stainless steel | Ir-coated beta-titanium | 0.338 ± 0.120 |

The individual wire pull tests are averages of the coefficient of kinetic friction measured along the wire, composed of 500 data points recorded. The same is true for the tests performed under lubricated conditions, the results of which are shown in Table 1b.

TABLE 1b

Coefficients of Friction for Various Bracket/Wire Couples, Wet Conditions

| Couple # | Bracket | Wire | Measured coefficient of friction (m)(Average ± Std. Dev.) |
|---|---|---|---|
| 1 | Bare stainless steel | Bare beta-titanium | 0.330 ± 0.181 (control) |
| 2 | Ir-coated stainless steel | Bare beta-titanium | 0.366 ± 0.200 |
| 3 | Bare stainless steel | Ir-coated beta-titanium | 0.231 ± 0.069 |

The literature value reported for the coefficient of friction at a 300 g normal load using brackets and wires of the same dimensions and materials as the control is 0.559±0.089. Coaxial springs, rather than ligatures, were used to exert the normal force on the bracket with the wire. Values reported for the same couple under human saliva are 0.224 ±0.032 and 0.286±0.29. Using stainless steel flats rather than ligatured brackets, the coefficient of friction measured in human saliva against TMA wire is 0.31 at a 33 g normal load.

The means of the friction coefficients of the various couples were compared by an analysis of variance. (E. L. Crow, F. A. Davis, M. W. Maxfield; Statistics Manual, Dover Publications, New York, (1960), pp. 118–126, 234–239) Average coefficients of friction for uncoated wire couples (control+coated bracket couples) were statistically the same under the analysis of variance F test ($p>0.05$). This was true whether the tests were under dry or Oralube-lubricated conditions. Similar results were found for average coefficients of friction for coated wire couples—they too were statistically the same, whether dry or wet ($p>0.05$).

Pooled data sets for coated wire and uncoated wire (control+coated bracket) couples were found to have large F quotients, far exceeding the tabulated values for $F_a$®-1, n-r) for $p<0.005$. The difference in the average coefficients of friction between coated wire and coated bracket couples was significant under both wet and dry conditions.

The difference between the coated wire couples and coated bracket couples was significantly different. The tests showed that the couples having the Ir-coated wire had far less "stick-slip" than couples having a bare wire and coated brackets. The qualitative term "stick-slip" is a way to describe the adhesive component of friction, which is due to the formation and rupture of interfacial bonds. Such bonds are the result of interfacial interatomic forces that depend on the degree of interpenetration of aspirates and surface composition. On a wire pull test, this manifests itself as increasing frictional forces building up steadily, then dropping sharply as the friction forces shear the weakest tangential planes at the areas of actual contact.

No attempts have previously been made to quantify stick-slip phenomena. In the present experiments, stick-slip was determined by measuring the sudden drops (slips) in the coefficient of friction of the wire along the bracket that occur when the system relieves itself of frictional force built up during a "stick". This was done by measuring the drop in coefficient of friction as it happens over a small distance of wire. Drops in coefficient of friction that were 0.005 or greater over 1 second of pull testing (at 1 cm/min) in all the individual friction tests were located. These drops are then averaged and the mean is found. These average sudden drops in coefficient of friction for each couple will be called the "average slip". As in the wire pull tests, individual stick-slip measurements are themselves averages of the large drops in the friction coefficient. The reduction in average slip produced by the presence of the Ir coating on the TMA wire is dramatic, especially under dry conditions. The measurements are averaged and are listed in Tables 2a and 2b below.

TABLE 2a

Average Slip for Bracket/Wire Couples (Dry conditions)

| Couple #(dry) | Bracket material | Wire material | Average Slip ± 1 Std.Dev. |
|---|---|---|---|
| 1 | Bare stainless steel (dry) | Bare beta-titanium (dry) | 0.143 ± 0.062 (control) |
| 2 | Ir-coated stainless steel | Bare beta-titanium | 0.127 ± 0.042 |
| 3 | Bare stainless steel | Ir-coated beta-titanium | 0.0292 ± 0.0069 |

TABLE 2b

Average Slip for Bracket/Wire Couples (Wet conditions)

| Couple #(wet) | Bracket material | Wire material | Average Slip ± 1 Std.Dev. |
|---|---|---|---|
| 1 | Bare stainless steel (wet) | Bare beta-titanium (wet) | 0.0404 ± 0.0128 (control) |
| 2 | Ir-coated stainless steel | Bare beta-titanium | 0.0409 ± 0.0142 |
| 3 | Bare stainless steel | Ir-coated beta-titanium | 0.0314 ± 0.0098 |

Analysis of variance testing was done for average slips of the various friction couples. The difference in average slips between bare wire couples versus coated wire couples, whether under dry or wet conditions, was very significant ($p<0.005$). Whether measured under either dry or wet conditions, Ir-coated wire couples showed significantly lower stick-slip than couples having bare, uncoated wires.

CONCLUSION

Iridium reduces the friction between the bracket and the wire when applied as a thin coating to orthodontic titanium-molybdenum alloy (TMA) wires. Both the overall coefficient of friction and the "stick-slip" were significantly reduced. This was true whether the wires and brackets were dry or wet with artificial saliva. Adhesion of the coatings to the wires, as evaluated by scratch testing, was good. Iridium coatings could be applied to TMA wires without embrittling them, making iridium attractive as a wire coating material on a commercial scale. Results of friction testing with coated brackets and uncoated TMA wires yielded friction and stick-slip that was not significantly different from control tests, regardless of the coating applied to the bracket. However, the iridium coating did not increase the amount of friction, and coated brackets have other advantages, such as improved appearance and wear properties.

Equivalents

While the invention has been disclosed in connection with the preferred embodiments shown and described in detail, various modifications and improvements will be apparent to one of ordinary skill in the art from the above description. Such equivalents are intended to be encompassed by the following claims.

What is claimed is:

1. A method of coating a metallic or ceramic orthodontic device comprising:
   applying to the device an adhesion layer having a thickness in the range of from about 100 Angstroms to about 10,000 Angstroms; and
   applying a friction-reducing metal layer to the adhesion layer.

2. The method of claim 1 wherein the metal is selected from the group consisting of iridium, platinum, palladium, rhodium, rhenium, gold, silver and blends or alloys of these.

3. The method of claim 1, wherein the adhesion layer comprises a material selected from the group consisting of chromium, titanium, nickel, palladium, a palladium-iridium blend, a chromium-iridium blend and blends or alloys of these.

4. The method of claim 1 wherein the friction-reducing layer is applied by a method selected from the group consisting of chemical vapor deposition, ion beam enhanced deposition, plasma-assisted chemical vapor deposition, cathodic arc deposition, sputtering and evaporation.

5. The method of claim 1, wherein the adhesion layer is applied by a method selected from the group consisting of chemical vapor deposition, ion beam enhanced deposition, plasma-assisted chemical vapor deposition, cathodic arc deposition, sputtering and evaporation.

6. The method of claim 1, wherein the adhesion layer has a thickness in the range of about from 500 Angstroms to about 5,000 Angstroms.

7. The method of claim 1 wherein the friction-reducing layer has a thickness in the range of from about 0.1 microns to about 5 microns.

8. The method of claim 7 wherein the friction-reducing layer has a thickness in the range of from about 0.5 microns to about 3 microns.

9. The method of claim 1, further comprising the step of applying an intermediate layer between the adhesion layer and the friction-reducing layer.

10. The method of claim 9 wherein the intermediate layer comprises iridium, chromium, titanium, nickel, palladium, or a blend or alloy of these.

11. The method of claim 1, wherein the adhesion layer comprises chromium, a blend of chromium and iridium or a blend of palladium and iridium.

12. The method of claim 1, wherein the adhesion layer and the friction-reducing layer are blended.

13. The method of claim 12 wherein the adhesion layer comprises a chromium-iridium blend.

14. The method of claim 1 further comprising the step of cleaning the surface of the device before applying the adhesion layer.

15. The method of claim 14 wherein the cleaning step is performed by ion sputtering using glow discharge or by an ion bombard process.

16. The method of claim 1, wherein the adhesion layer comprises chromium, and wherein the adhesion layer is applied by sputtering the chromium at a bias of from about 1 volt to about 10,000 volts, in an inert gas atmosphere at a pressure of from about 0.1 mTorr to about 100 mTorr.

17. A method of coating a metallic or ceramic orthodontic device comprising:
   applying a chromium adhesion layer to the device; and
   applying a friction-reducing metal or ceramic layer to the adhesion layer;
   wherein the adhesion layer is applied by sputtering the chromium at a bias of from about 1 volt to about 10,000 volts, in an inert gas atmosphere at a pressure of from about 0.1 mTorr to about 100 mTorr.

18. A dental article comprising an adhesion coating having a thickness in the range of from about 100 Angstroms to about 10,000 Angstroms and a friction-reducing metal coating on the adhesion coating.

19. The dental article of claim 18 comprising an orthodontic archwire, bracket, retainer or palate expander.

20. The dental article of claim 18 wherein the metal comprises iridium, platinum, palladium, rhodium, rhenium, gold, silver or a blend or alloy of these.

21. The dental article of claim 20 wherein the metal comprises iridium.

22. The dental article of claim 18 wherein said friction-reducing coating is between about 0.1 microns and about 5 microns thick.

23. The dental article of claim 22 wherein said friction-reducing coating is between about 0.5 microns and about 3 microns thick.

24. The dental article of claim 18, wherein said adhesion coating comprises a material selected from the group consisting of chromium, titanium, nickel, palladium, a palladium-iridium blend, a chromium-iridium blend and blends or alloys of these.

25. The dental article of claim 24 wherein the adhesion coating comprises chromium, a blend or chromium and iridium or a blend of iridium and palladium.

26. The dental article of claim 25 wherein said adhesion coating is between about 500 Angstroms and about 5,000 Angstroms thick.

27. The dental article of claim 18 further comprising an intermediate layer disposed between said adhesion coating and said friction-reducing coating.

28. The dental article of claim 27 wherein said intermediate layer comprises chromium, iridium, titanium, nickel, palladium or a blend or alloy of these.

* * * * *